United States Patent [19]
Woods et al.

[11] Patent Number: 5,190,560
[45] Date of Patent: Mar. 2, 1993

[54] INSTRUMENT FOR LIGATION AND CASTRATION

[76] Inventors: John B. Woods, 10919 S. Sandusky, Tulsa, Okla. 74137; Wayne Porter, Rte. 1, Bowie, Tex. 76230

[21] Appl. No.: 718,508

[22] Filed: Jun. 20, 1991

[51] Int. Cl.⁵ ............................................. A61B 17/12
[52] U.S. Cl. .................................. 606/137; 606/139; 606/143; 606/142
[58] Field of Search ............... 606/135, 137, 120, 142, 606/143, 144, 139, 228, 136, 1

[56] References Cited

U.S. PATENT DOCUMENTS

| | | | |
|---|---|---|---|
| 3,006,344 | 10/1961 | Vogelfanger | 606/143 |
| 3,675,688 | 7/1972 | Bryan et al. | 606/143 X |
| 3,954,108 | 5/1976 | Davis | 606/142 |
| 4,050,465 | 9/1977 | Périssé | 606/139 |
| 4,196,836 | 4/1980 | Becht | 606/143 X |
| 4,815,465 | 3/1989 | Alvarado | 606/135 |
| 4,817,602 | 4/1989 | Beraha | 606/157 |
| 4,929,239 | 5/1990 | Braun | 606/142 |
| 5,035,692 | 7/1991 | Lyon et al. | 606/143 |

Primary Examiner—Peter A. Aschenbrenner

[57] ABSTRACT

An instrument for castration by ligating and severing blood and seminal vessels. A pistol-shaped tool comprises a hollow body forming a barrel and a hand grip. A yoke pivotally mounted in the cavity of the grip is pivotally connected to a trigger, ligating means and severing means. The vessel to be ligated and severed is positioned in a slotted area at the muzzle of the barrel. The initial pulling of the trigger toward the grip causes blade guards connected to the severing means to surround the vessel or vessels. Further movement of the trigger toward the grip actuates the ligating means to push a ligature from a ligature container and around the vessels. The ligature is forced through ligature compressors which press the locking ligature onto the vessels. Final movement of the trigger toward the grip moves the severing means to force a blade through the vessels.

17 Claims, 6 Drawing Sheets

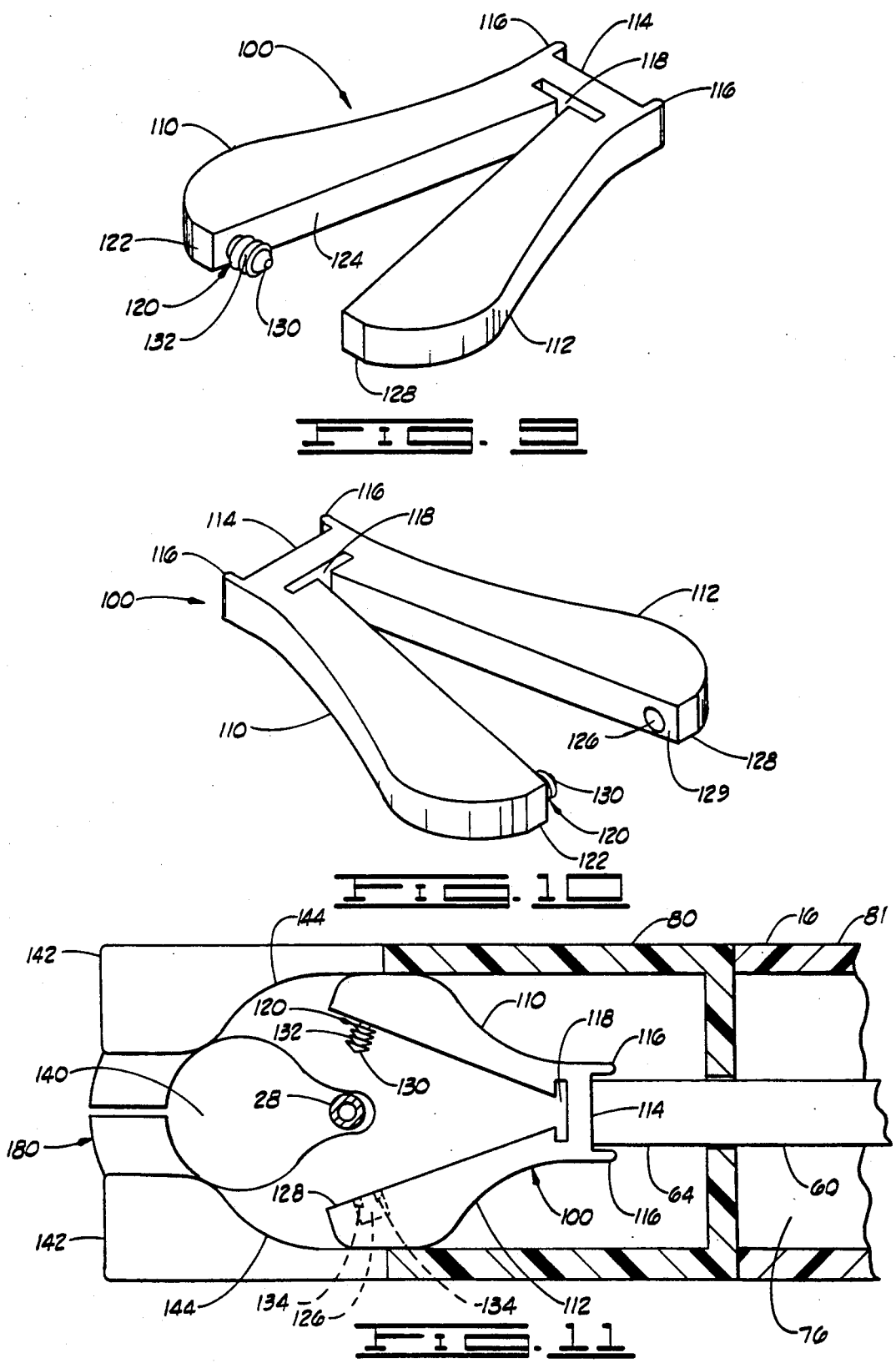

INSTRUMENT FOR LIGATION AND CASTRATION

FIELD OF THE INVENTION

The present invention relates to improvements in instruments for the castration of animals and particularly the castration of bull calves.

SUMMARY OF THE INVENTION

The castration of bull calves is usually performed by holding the animal as steady as possible and cutting the testicular sac and vessels with an open blade. Because of the nervous condition of the animal and the proximity of an open blade to unprotected body parts of the animal and the knife-wielder, there exists a risk of injury to both man and animal.

The present invention comprises an instrument and a process for performing the dual function of ligating and severing vessels in the castration of animals. The invention is a pistol-shaped instrument with a double-action trigger. The first action of the trigger applies a ligature to the vessel and the second action thrusts the cutting blade through the vessel to sever the vessel and thereby castrate the animal.

One advantage of the present invention is the shape and weight of the instrument. The pistol grip and light weight allow the instrument to be used effectively with one hand. The chance of injury is thereby reduced because the free hand can be used to expose the vessel to be out or to steady oneself and the animal.

Another advantage of the invention is to enclose the cutting blade as much as possible in order to minimize human and animal exposure to the sharp edge. Enclosing the blade edge further reduces the risk of injury in the event that the animal rears or kicks during the cutting process.

Yet another advantage of the invention is to ligate the animal's vessel prior to the severance of the vessel in order to minimize bleeding by the animal. In this manner, the animal recovers more quickly and is less likely to develop a debilitating or fatal condition as a result of hemorrhaging. Suffering of the animal and the cost of caring for a sick or dying animal are thereby avoided.

If the animal is being raised to be sold at market, the quicker recovery from castration allows faster weight gain and a more economical cattle operation. Reducing animal fatalities resulting from castration, of course, saves money in the form of replacement costs and the expense of disposing of the dead animals.

BRIEF DESCRIPTION OF THE DRAWINGS

FIG. 9 is a perspective view of a ligature showing the male face of the ligature.

FIG. 10 is a perspective view of a ligature showing the female face of the ligature.

FIG. 11 is a top view, partially in section, of a ligature and ligature driver before the ligature is compressed around a vessel.

DETAILED DESCRIPTION OF THE PREFERRED EMBODIMENT

Figure 1:
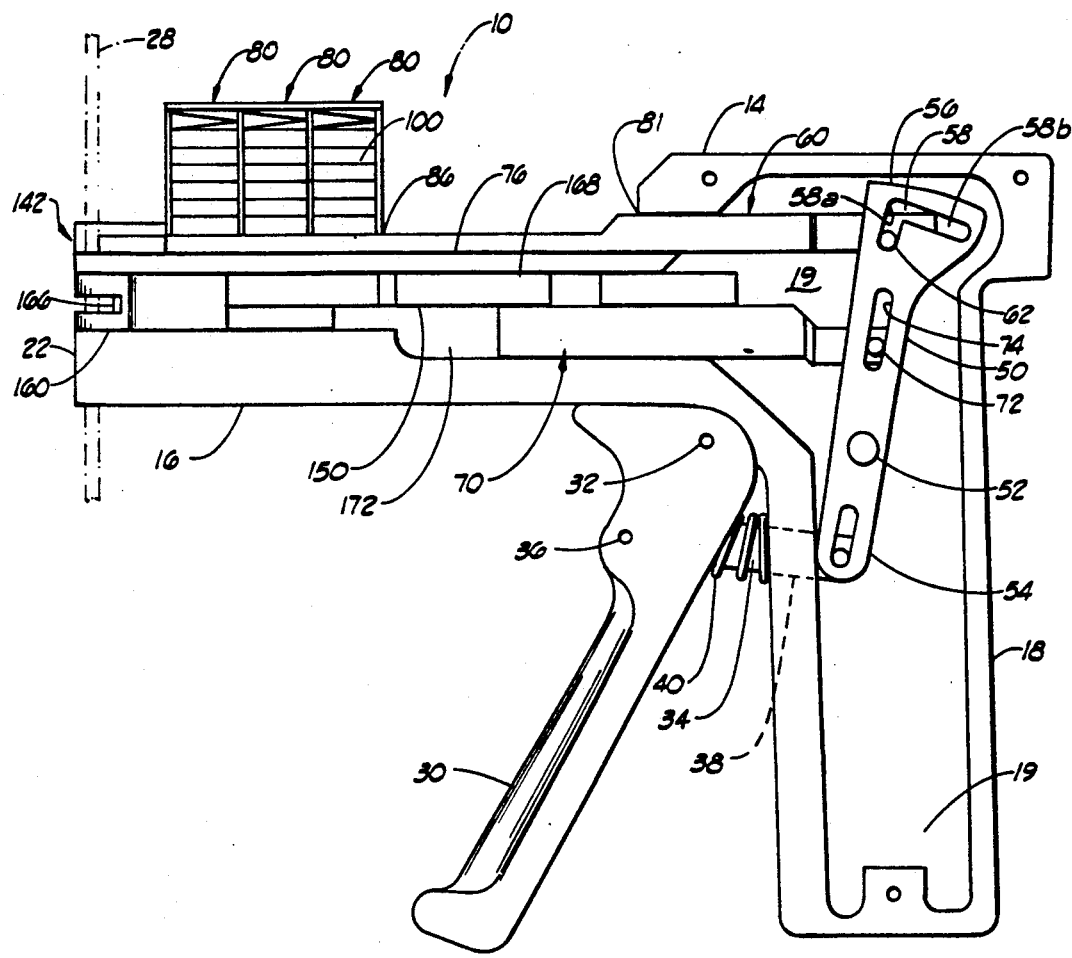
FIG. 1 is a side view of the instrument with one side removed to show the inner workings of an instrument constructed in accordance with the invention.

Referring to the drawings in detail, and particularly FIG. 1, reference character 10 generally designates a veterinary instrument constructed in accordance with the present invention. The instrument 10 basically comprises a pistol-shaped body 14, which includes a barrel 16 and a grip 18. The barrel 16 and grip 18 are hollow to form a cavity 19 in the body 14 which houses the inner workings of the instrument.

The end of the barrel 16 forms a muzzle 22, which opens into the cavity 19 and, as described hereinafter, is formed to receive the blood vessel or seminal vessel 28 (shown in dashed lines in FIG. 1) to be ligated and severed. A trigger 30 is pivotally attached to the body 14 at a point designated by reference numeral 32. The trigger 30 and grip 18 are sized and shaped to be grasped and operated with one hand.

A trigger rod 34 is attached to the trigger 30 at a medial point 36 of the trigger 30 and extends through an opening 38 in the grip 18 into the cavity 19 of the grip 18. In a preferred embodiment, the trigger rod 34 is pivotally attached to the trigger 30, but the instrument operates suitably if such attachment is rigid.

A trigger spring 40 is preferably disposed around the trigger rod 34 between the trigger 30 and the grip 18. The trigger spring 40 provides a bias which returns the device to the rest, or withdrawn, position as shown in FIG. 1.

The action of the instrument is largely controlled by a yoke 50, which is pivotally secured in the cavity 19 of the grip 18 at a medial point 52 of the yoke 50. The yoke 50 is basically a flat bar with openings or slots for the trigger action, the ligating action and the severing action of the instrument. The end of the trigger rod 34 extending into the cavity 19 of the grip 18 is pivotally attached to the trigger end 54 of the yoke 50.

Referring still to FIG. 1, the other end of the yoke 50, the ligating end 56, widens to the side away from the barrel 16 and contains a substantially L shaped ligating slot 58. A pin 62, rigidly formed at one end of a ligature driver 60, is slidingly disposed in the ligating slot 58. One leg 58a of the L-shaped ligating slot 58 extends along the length of the yoke 50 and the second leg 58b extends along the width of the yoke 50 in a direction away from the barrel 16.

At a point between the pivot 52 of the yoke 50 and the ligating slot 58, a blade driver 70 is pivotally attached to the yoke 50. A pin 72, rigidly formed at one end of the blade driver 70, is pivotally disposed through the blade driver slot 74 of the yoke 50.

The action of the trigger 30 and yoke 50 is best visualized by referring to FIG. 1. As the trigger 30 is pulled toward the grip 18, the yoke 50 moves in a counter-clockwise direction about the pivot 52 of the yoke 50. The movement of the yoke 50 at the ligating end 56 and at the blade driver pin 72 is counter-clockwise toward the muzzle 22 as the trigger 30 is pulled toward the grip 18.

By virtue of attachment to the yoke 50, the ligature driver 60 and blade driver 70 generally move toward the muzzle 22 as the trigger 30 is pulled toward the grip 18. Conversely, as the trigger 30 is released and forced away from the grip 18 by the trigger spring 40, the ligature driver 60 and blade driver 70 generally move away from the muzzle 22. The ligature driver 60 and blade driver 70 extend from the yoke 50 along the length of the barrel 16 so that the movements toward and away from the muzzle 22 are in the direction along the length of the barrel 16.

In a preferred embodiment, the ligature driver 60 extends along the outside top surface 76 of the barrel 16 and the blade driver 70 extends lengthwise within the cavity 19 of the barrel 16.

It should be noted that the movement of the yoke 50 causes a series of actions by the ligature driver 60 and the blade driver 70. With the initial movement of the trigger 30 toward the grip 18, the end of the ligature driver 60 moves in the leg 58a of the ligating slot 58 as the ligature driver 60 moves toward the muzzle 22. During this same time, the blade driver 70 is moving forward (although a lesser distance) to cause the blade guards to encircle the vessel 28 as discussed hereinafter.

Upon further movement of the trigger 30 toward the grip 18, the ligature driver 60 is forced toward the muzzle 22 by the yoke 50. This forward movement of the ligature driver 60 forces a ligature 100 around the vessel 28 to ligate the flow of fluid through the vessel 28. By the time the ligature 100 is applied, the blade guards have encircled the vessel 28 and the severing blade is moving toward the vessel 28 as will be discussed in detail below.

Turning now to the dispensing and application of the ligating ligatures 100, FIG. 1 shows ligature containers 80 mounted upon the top outside surface 76 of the barrel 16, such that the ligature driver 60 extends into the ligature containers 80. The ligature driver 60 protrudes from an opening 81 in the body 14 at the top surface 76 of the barrel 16 nearest the grip 18. The travel of the ligature driver 60 is maintained in a centered position along the length of the barrel 16 by the walls of the opening 81 in the body 14.

Figure 3:
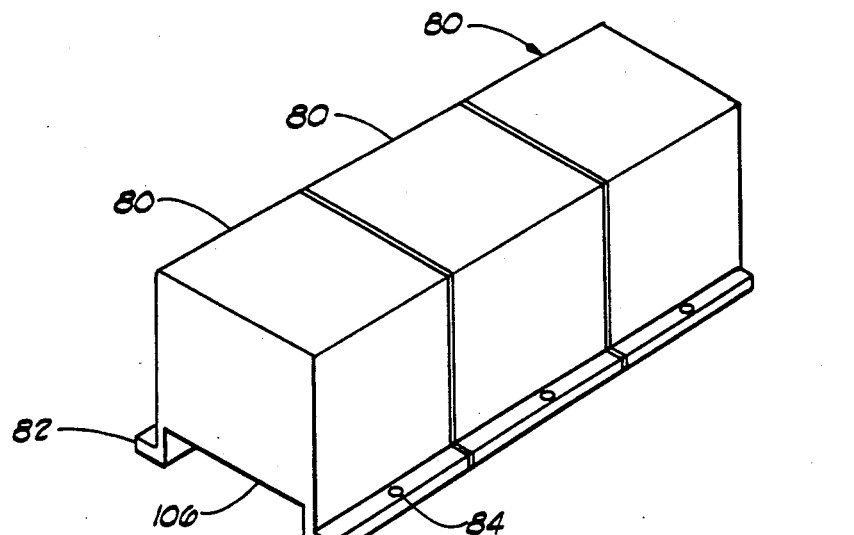
FIG. 3 is a perspective view of the ligature containers.

As FIGS. 1 and 3 illustrate, the ligature containers 80 are roughly cubical in shape. Preferably, up to three ligature containers 80 may be removably attached to the barrel 16 of the instrument 10.

Figure 2:
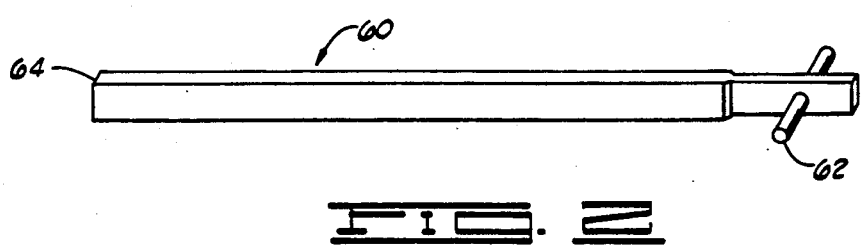
FIG. 2 is a perspective view of the ligature driver.

FIG. 2 shows the structure of the ligature driver 60, which is essentially a flat, elongated bar. The ligature driver 60 has the rigid pin 62 extending from one end for pivotal attachment through the ligating slot 58 of the yoke 50. The muzzle end 64 of the ligature driver 60 contacts a ligature to push the ligature from the ligature container 80 as will be described in detail below.

Figure 4:
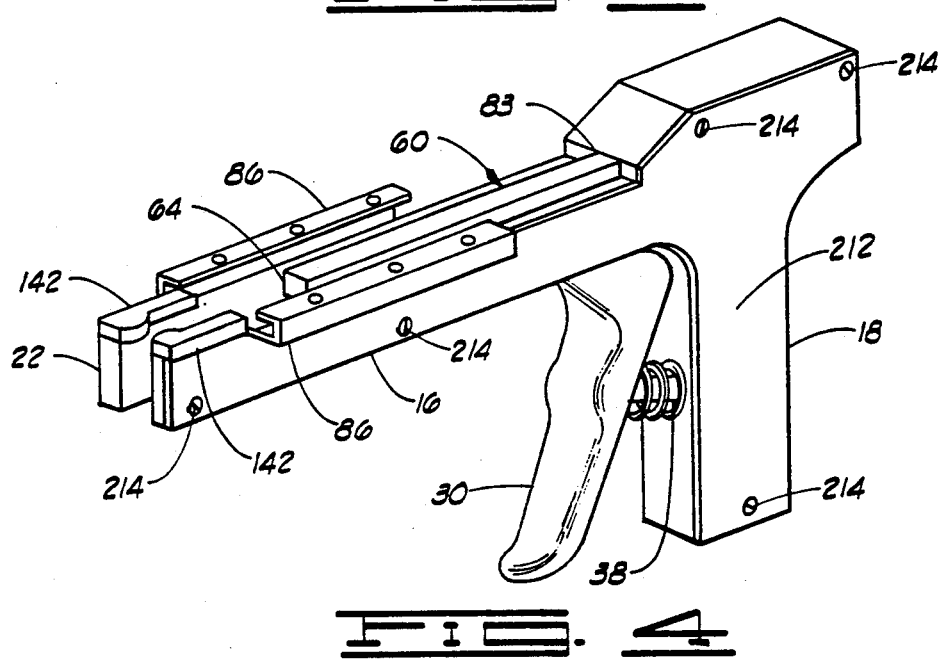
FIG. 4 is a perspective view of the instrument with the ligature containers removed.
Figure 5:
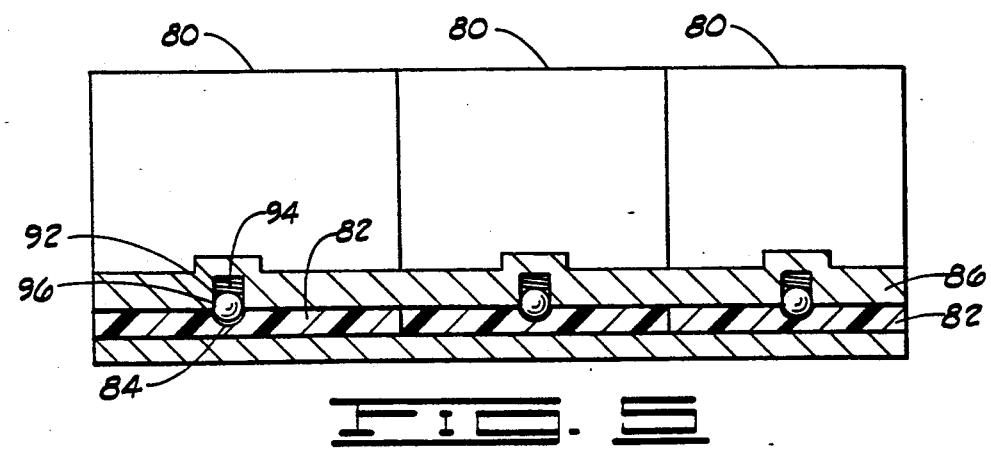
FIG. 5 is a cross sectional view of the means for attaching the ligature containers to the barrel of the instrument.

FIGS. 3-5 show in detail the preferred device for removably attaching the ligature containers 80 to the barrel 16. As best shown in FIG. 3, each ligature container 80 has its lower edges 82 protruding outwardly from each side and extending the length of the ligature container 80. Centrally located on the top surface of each protruding edge 82 is an indentation 84. The indentation 84, a rounded groove or hole, is shaped to receive the securing ball of the barrel 16, as described hereinafter.

Referring now to FIG. 4, a channel 86 having a basically C-shaped cross-section is rigidly attached to each upper side of the barrel 16 and extends outwardly from the side of the barrel 16. The channel 86 on each side of the barrel 16 is sized and shaped to receive the protruding edge 82 of the ligature container 80.

As best illustrated in FIG. 5, the upper portion of the channel 86 contains securing ball mechanisms to lock the ligature containers 80 in the channel 86. The securing mechanism consists of a recess 92, a spring 94 and a ball 96. The opening of the recess 92 is large enough that a portion of the ball 96 protrudes from the surface of the channel 86 and the ball 96 is able to rotate within the recess 92. The ball spring 94 is located in the recess 92 behind the ball 96 to provide a bias on the ball 96 to protrude.

The ligature container 80 is installed on the barrel 16 by matching the protruding edges 82 of the ligature container 80 with the channel 86 at the end of the channel 86 away from the muzzle 22. The ligature container 80 is then pushed toward the muzzle 22 until a securing ball 96 of the channel 86, under the bias of the ball spring 94, protrudes into an indentation 84 of the ligature container 80. A nudge on the ligature container 80 rotates the securing ball 96 or overcomes the bias of the ball spring 94 and the ligature container 80 can be moved to another position of the channel 86 or from the channel 86 completely.

This ball and indentation mechanism allows quick and easy attachment and removal of ligature containers 80 to the barrel 16 of the instrument 10. Although this mechanism is preferred, other suitable snap-in or rigid means of attachment are acceptable.

Figure 6:
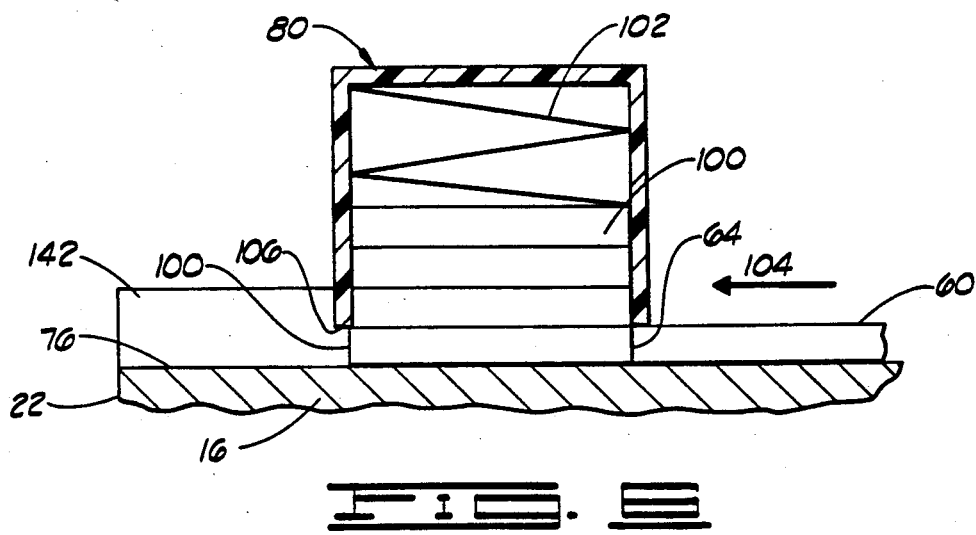
FIG. 6 is a cross sectional view of a ligature container and ligature driver before a ligature is pushed from the ligature container.

Each ligature container 80 is basically a hollow cube-shaped structure. FIG. 6 shows a number of ligatures 100 stacked within a ligature container 80. A ligature spring 102 between the stack of ligatures 100 and the top inner surface of the ligature container 80 provides a bias to push the stack of ligatures 100 to the lower edge of the ligature container 80. The lower portion of the ligature container 80 may include a shoulder (not shown) shaped to receive the bottom ligature 100 to ensure that the ligatures are dispensed one at a time.

In a preferred embodiment, the bottom and openings of the ligature container 80 are sealed with a bacterial or microorganism barrier (not shown) which is removed prior to use. This seal allows the ligatures 100 to be maintained in a sterile environment in the ligature container 80 until required for use.

Figure 7:
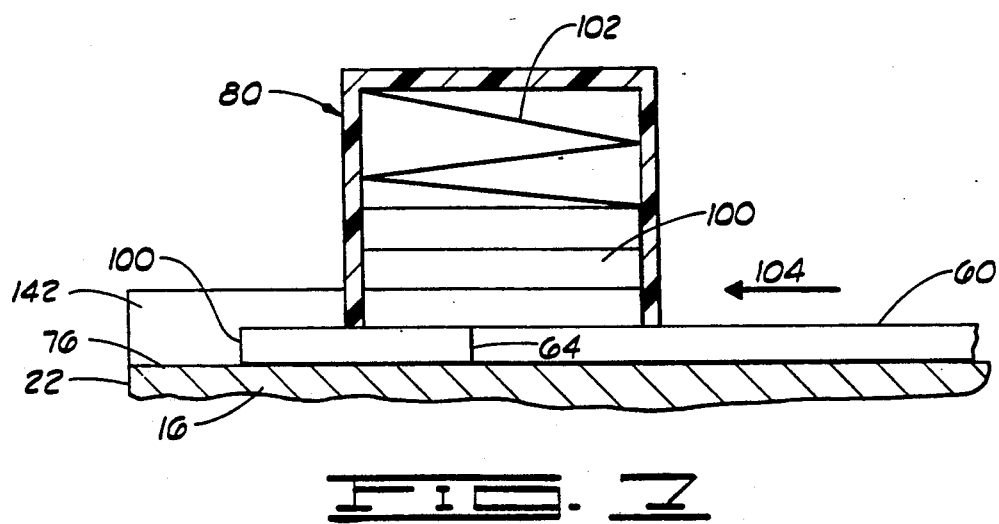
FIG. 7 is a cross sectional view of the ligature container and ligature driver of FIG. 6 with a ligature pushed partially from the ligature container.
Figure 8:
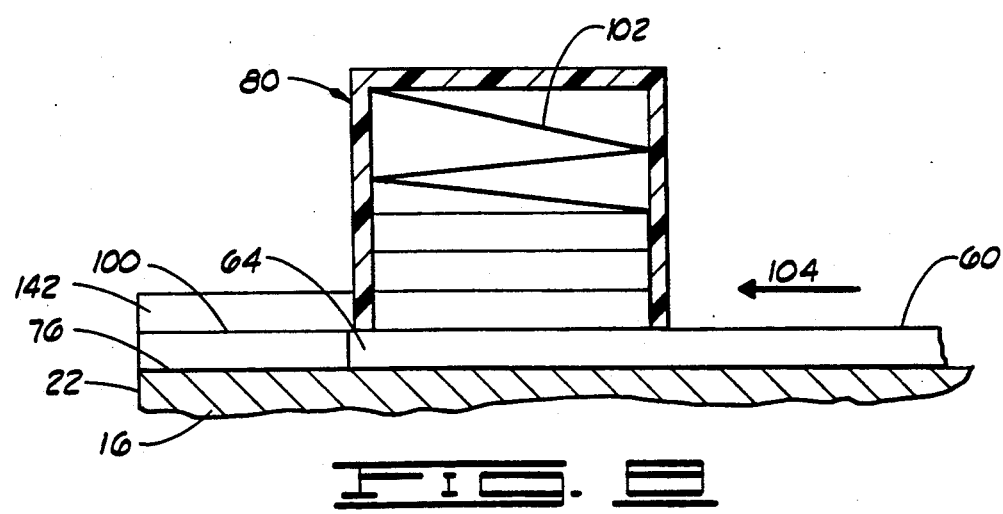
FIG. 8 is a cross sectional view of the ligature container and ligature driver of FIG. 7 with a ligature pushed completely from the ligature container.

FIGS. 6–8 show how the ligature driver 60 forces a ligature 100 from the end ligature container 80. The bias of the ligature spring 102 ensures that the bottom ligature 100 in the stack rests against the top surface 76 of the barrel 16. As the ligature driver 60 moves toward the muzzle 22, as indicated by direction arrow 104, the lower ligature 100 is pushed through the ligature opening 106 and out of the ligature container 80.

When the ligature driver 60 is retracted sufficiently toward the grip 18, the bias of the ligature spring 102 forces the next ligature to the top surface 76 of the barrel 16. The process is repeated until all of the ligatures 100 in the end ligature container 80 have been used. Then the end, empty ligature container 80 is removed and a reserve ligature container 80 is moved to the position nearest the muzzle 22 as described hereinabove.

In a preferred embodiment, up to three ligature containers 80 may be attached to the barrel 16 and each ligature container 80 holds up to five ligatures 100. Other combinations and arrangements of ligatures 100 and ligature containers 80 may be utilized within the spirit and intent of the invention.

FIGS. 9–11 illustrate the construction of the ligatures 100. The ligatures 100 are preferably made of an absorbable material, which dissolves in the animal's body after sufficient time has passed for the severed vessel 28 to heal together. Although non-dissolving, materials such as non-absorbable plastic, metal or other substances with suitable properties may be utilized.

As shown in FIGS. 9 and 10, the ligature 100 consists of a male leg 110 and a female leg 112 joined at a base 114. At each side of the base 114 are ears 116 which act as a guide for contact of the ligature driver 60 with the ligature 100. The spacing of the base 114 between the ears 116 should be wide enough to receive the end of the ligature driver 60 which extends into the ligature container 80. The ears 116 extend the full vertical distance of the ligature 100 at each side of the base 114.

At the side of the base 114 opposite the ears 116 is an opening 118 which acts as a hinge area and allows the male leg 110 and the female leg 112 to flex apart or together. Each ligature 100 is constructed to be in an open position initially. Moreover, the legs 110 and 112 of the ligature 100 should be far enough apart to receive the vessel 28 to be ligated.

The male leg 110 includes a locking protrusion 120 near the distal end 122 of the male leg 110 and extending from the male surface 124 facing the female leg 112. The female leg 112 includes a locking aperture 126 near the distal end 128 of the female leg 112 and extending into the female surface 129 facing the male leg 110.

The locking protrusion 120 and locking aperture 126 of the ligature 100 are located such that the locking protrusion 120 penetrates into the locking aperture 126 when the male leg 110 and female leg 112 are pressed together. To facilitate such penetration, the tip 130 of the locking protrusion 120 is rounded to form a dull point.

As best shown in FIGS. 9 and 11, a set of saw-tooth locking rings 132 protrude outwardly from the circumference of the locking protrusion 120. To complete the ligature-locking mechanism, the opening of the locking aperture 126 is uniformly restricted around its circumference by a locking flange 134. As illustrated in FIG. 11, the locking flange 134 is sized and shaped to interlock with the saw-tooth rings 132 of the locking protrusion 120.

Figure 12:
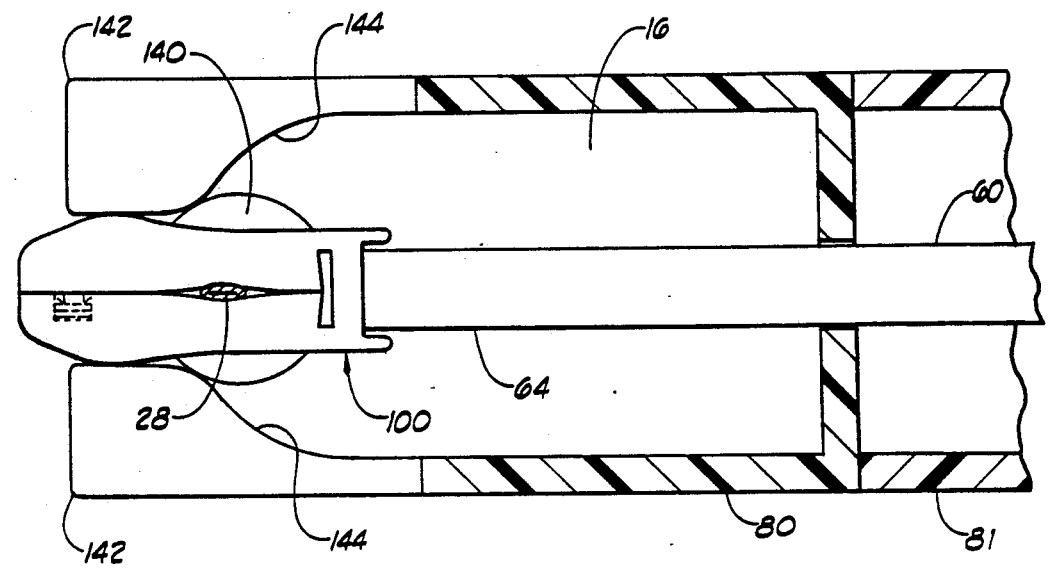
FIG. 12 is a top view of a ligature and ligature driver of FIG. 11 after the ligature is compressed around a vessel.

FIGS. 11 and 12 best show a preferred means for applying a ligature 100 to a blood or seminal vessel 28. The muzzle 22 includes a vertical opening 140 in which the vessel 28 to be ligated and severed is positioned. The vertical opening 140 opens to the end of the muzzle and should extend from the top to the bottom of the barrel 16 as shown in FIGS. 1 and 4. The teardrop cross-sectional shape of FIG. 11 is preferred for the vertical opening 140, but a V-shape or any other suitable shape is acceptable.

A ligature 100 is applied to the vessel 28 as the ligature driver 60 forces the ligature 100 through a pair of ligature compressors 142 (FIGS. 11 and 12) located along the top surface 76 of the barrel 16. The ligature compressors 142 are rigidly attached to the top of the muzzle 22, one ligature compressor 142 on each side of the barrel 16, such that the ligature driver 60 forces the ligature 100 between the two ligature compressors 142.

The surfaces 144 of the ligature compressors 142 which engage the ligature 100 are uniformly curved such that the space between the legs 110 and 112 of the ligature 100 narrows as the ligature 100 is pushed through the ligature compressors 142. As shown in FIG. 11, the path of the ligature 100 upon entering the ligature compressors 142 should be wide enough for the open ligature 100 to pass around the vessel 28. At the position wherein the ligature driver 60 is nearest the muzzle 22, the path of the ligature 100 between the ligature compressors 142 should be narrow enough to force the ligature 100 into a locked position around the vessel 28. FIG. 12 illustrates the ligated vessel 28 with the ligature 100 in a locked position. After a ligature 100 is secured around the vessel 28, the pin 62 of the driver 60 enters the portion 58b of slot 58, such that the yoke 50 can continue to pivot for the severing operation as described below.

In a preferred embodiment, the ligature compressors 142 extend upwardly from the top of the barrel 16 for a distance which approximates the thickness of a ligature 100. A greater or lesser distance is acceptable without adversely affecting the operation of the invention.

While the instrument is ligating the blood and seminal vessels 28, the instrument 10 is also preparing to sever those vessels 28. As described above and shown in FIG. 1, the blade driver 70 forces the blade 150 forward and through the vessel or vessels 28.

Figure 14:
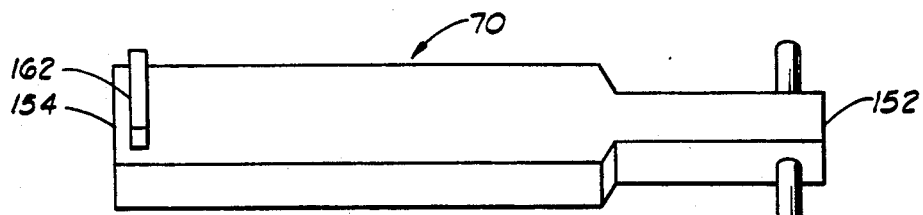
FIG. 14 is a perspective view of the blade driver of the instrument.

FIG. 14 best illustrates the construction of the blade driver 70. The blade driver 70 is essentially a flat, rigid bar which is shaped to attach pivotally at end 152 to the yoke 50 and to attach removably at the other end 154 to the blade 150. The end 152 is formed with the rigid pin 72 extending from the blade driver 70 at a right angle to the length of the blade driver 70. The blade driver 70 tapers toward end 152 in order for the blade driver pin 72 to fit into the blade driver pin hole 74 of the yoke 50.

Figure 13:
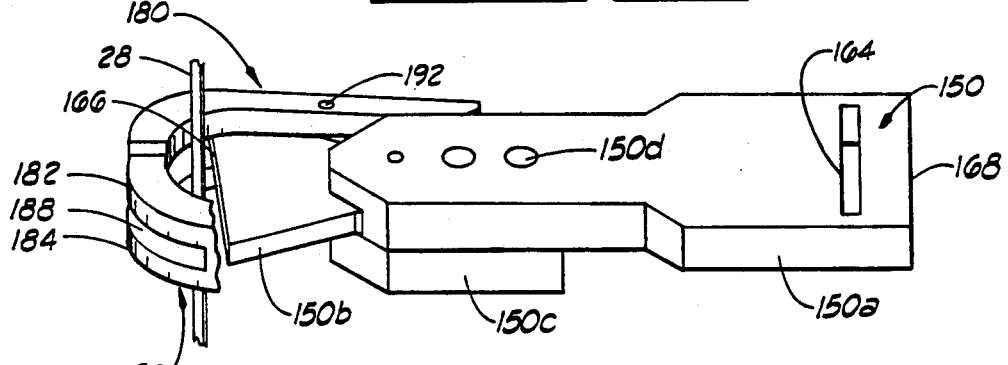
FIG. 13 is a perspective view of the blade guards and severing blade of the instrument with portions broken away for clarity.

A connecting bar 162 protrudes from the top surface of the blade driver 70 proximate to the end 154. The connecting bar 162 is sized and shaped to fit in a slot 164 in the blade 150, as shown in FIGS. 13 and 14 and described hereinafter. Preferably, the slot 164 and the cross-section of the connecting bar 162 are rectangular to prevent wobbling or pivoting of the blade 150 with respect to the blade driver 70, but any suitable shape for secure connection is acceptable.

Although a more permanent connection of the blade 150 and blade driver 70 would function properly, it is desirable that the blade 150 be readily removable in order to replace, clean and sharpen the blade 150.

As illustrated in FIG. 1, the blade 150 is disposed lengthwise in the barrel 16 with its sharpened end 166 toward the muzzle 22 and the slotted end 168 connected to the blade driver 70. The lower portion of the barrel 16 includes a recessed area 172 in the cavity 19 to allow the blade driver 70 to move freely toward the muzzle 22.

As shown in FIG. 13, the blade 150 is constructed in three parts. The main body portion 150a contains the slot 164. The cutting portion 150b, which has the sharpened end 166, is secured to the main body portion 150a by a third portion 150c secured to the main body portion by screws or the like 150d.

Referring now to FIGS. 1 and 13, the blade 150 is shown in conjunction with a pair of blade guards 180. Pivotally attached inside the barrel 16 near the muzzle 22, the blade guards 180 mirror and oppose each other on each side of the blade 150. The blade guards 180 guide the blade 150 through the cutting area and also protect the animal and the instrument operator from the sharp edge of the blade 150.

Figure 15:
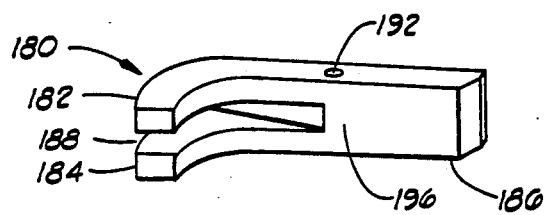
FIG. 15 is a perspective view of a blade guard.

As best illustrated by FIG. 15, each blade guard 180 includes upper and lower surrounding members 182 and 184 joined at a base 186. Although a curved shape is preferred for the surrounding members 182 and 184, any shape which encloses about the vessel 28 and allows the blade 150 to pass through the cutting area is acceptable. The upper and lower surrounding members 182 and 184 are substantially parallel to each other and separated by a space 188 through which the blade 150 travels.

The pivot point of the blade guards 180 is a hole 192 through the base 186, as shown in FIGS. 15-18. A pin 194 extends from the lower inside surface of the barrel 16 through each hole 192 to pivotally attach the blade guards 180 within the barrel 16.

Figure 16:
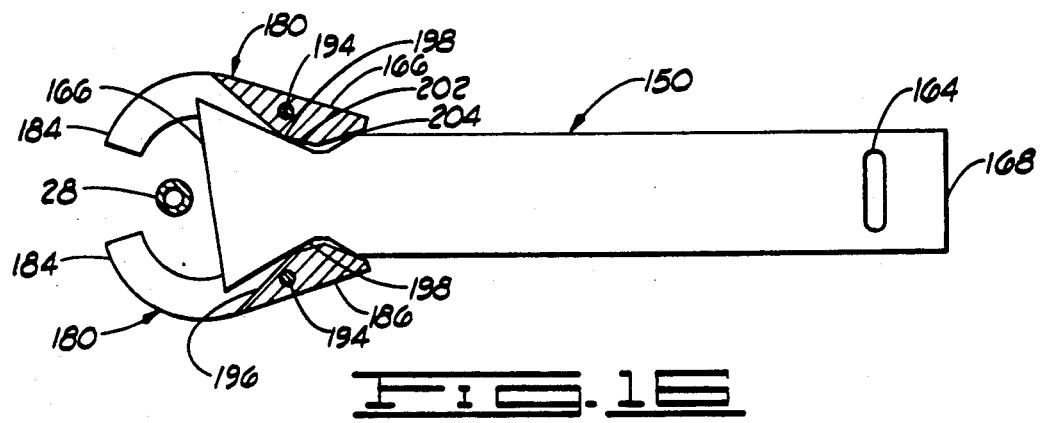
FIG. 16 is a schematic top view, partially in section, of the blade guards and blade at a position wherein the vessel is neither encircled nor severed.
Figure 17:
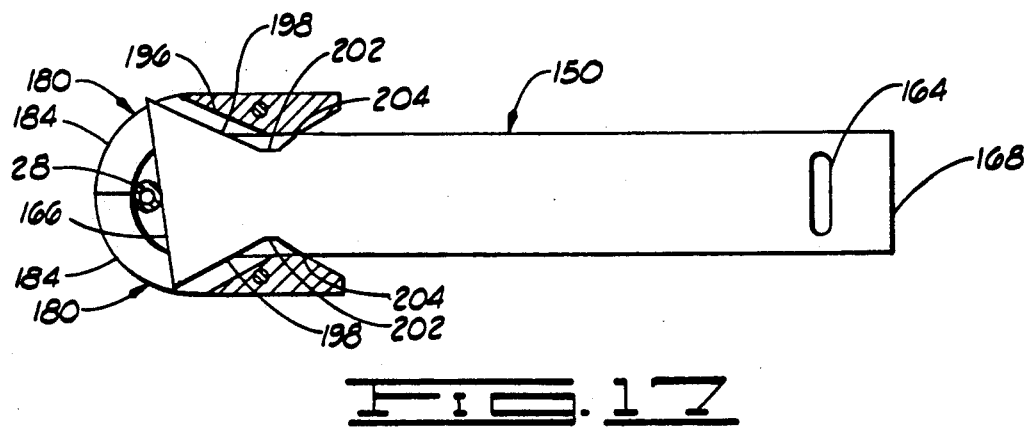
FIG. 17 is a schematic top view, similar to FIG. 16, of the blade guards and blade at a position wherein the vessel is encircled but not yet severed.
Figure 18:
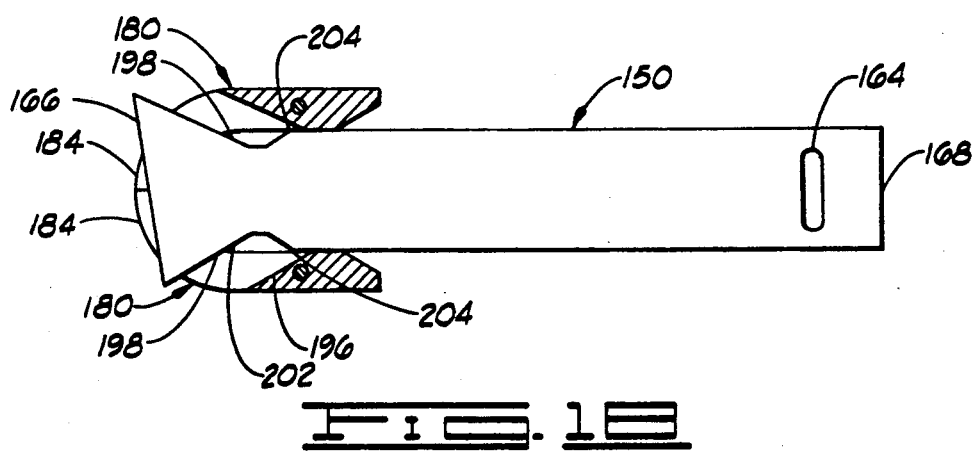
FIG. 18 is a schematic top view, similar to FIGS. 16 and 17, of the blade guards and blade at a position wherein the vessel is both encircled and severed.

FIGS. 16-18 illustrate the structure and operation of the blade guards 180 and the blade 150. Each blade guard 180 has a curved surface 196 to make contact with the side edge 198 of the blade 150.

The blade 150 is uniquely shaped to cooperate with the curved surface 196 of the blade guards 180. The blade 150 is widest at the sharpened end 166 and curvingly narrows to a throat 202. From the throat 202, the blade 150 curvingly widens to form a shoulder 204. The blade 150 then has a uniform width from the shoulder 204 to the slotted end 168.

In operation, the coordinating shapes of the blade 150 and blade guards 180 cause the movement of the blade 150 to open and close the surrounding members 182 and 184 of the blade guards 180. FIG. 16 illustrates the rest or withdrawn position. The surrounding members 182 and 184 of the blade guard 180 are open, the blade 150 is toward the base 186 of the blade guards 180, and the vessel 28 is positioned in the cutting area between the surrounding members 182 and 184. (The upper surrounding members 182 are cut away in FIGS. 16-18 to reveal the blade 150 and the curved surface 196 of the base 186 of the blade guards 180.)

FIG. 17 illustrates the blade 150 in a position partially advanced toward the vessel 28. As the blade 150 moves toward the vessel 28, the shoulders 204 of the blade 150 push the base 186 of each blade guard 180 in an outward direction. This spreading of the bases 186 of the blade guards 180 results in an inward, or closing, movement of the surrounding members 182 and 184.

In FIG. 18, the blade 150 has moved completely through the vessel 28 and severed the vessel. The blade 150 is fully extended toward the muzzle 22 and the blade guards 180 remain closed. The blade guards 180 have not moved in the progression from FIG. 17 to FIG. 18 because the width of the blade 15 is uniform during this phase of movement.

The withdrawal of the blade 150 results in the reverse sequence of movement, from the position of FIG. 18 to the position of FIG. 16. The surrounding members 182 and 184 are forced open as the shoulders 204 pass the bases 186 of the blade guards 180 and the increased width of the sharpened end 166 pushes the surrounding members 182 and 184 outward.

As mentioned above, an advantage of the invention is that the blade 150 can be readily removed for replacement, cleaning or sharpening. As illustrated in FIG. 1, access to the blade 150 is provided by removing one side plate 212 (shown in FIG. 4) of the instrument 10. The side plate 212 is preferably secured to the instrument 10 by means of screws 214.

After removal of the side plate 212, the connecting bar 162 of the blade driver 70 can be detached from the slot 164 in the blade 150. The blade 150 can then be moved toward the muzzle 22 between the blade guards 180 and out of the barrel 16. A blade 150 can be installed by reversing the steps just described.

The sizing of the various operating parts is such that during the initial movement of the trigger 30, the blade guards 180 are closed around the vessel 28; then a ligature 100 is applied on the vessel 28; then the blade severs the vessel 28. Upon release of the trigger 30, the blade guards 180 retract; the blade 150 retracts; and the ligature driver 60 retracts to a starting position—all by action of the return spring 40.

Changes may be made to the construction, operation, and arrangement of the various parts, elements, steps and procedures described herein without departing from the spirit and scope of the invention as defined in the following claims.

What is claimed is:

1. An instrument for placing a ligature on a tubular vessel and for severing the tubular vessel and associated structures, the instrument comprising:
   a pistol-shaped body forming a barrel and a grip, wherein the barrel has a muzzle with a muzzle opening therethrough for receiving tubular vessels and the body is formed with a cavity extending from the muzzle opening through the barrel and into the grip;
   a trigger operatively connected to the body, wherein the trigger includes a trigger rod extending from the trigger through the grip and into the cavity;
   a yoke mounted at a medial pivot point thereof within the cavity and having a trigger end and a ligating end, wherein the trigger end is pivotally connected tot he end of the trigger rod extending into the cavity;
   a ligature driver connected to the ligating end of the yoke and slidingly disposed along the upper length of the barrel, the ligature driver adapted to move toward the muzzle and back in response to the pivoting movement of the yoke;
   a pair of ligature compressors attached to the barrel on opposing sides of the muzzle opening with a space between the ligature compressors, the space between the ligature compressors narrowing toward the muzzle of the barrel to compress a ligature around a tubular vessel positioned in the muzzle opening as the ligature driver pushes the ligature toward the muzzle between the ligature compressors;

a blade driver pivotally attached to the yoke at a point between the ligating end and the pivot point of the yoke, the blade driver having a muzzle end extending into the barrel and moving lengthwise within the barrel toward the muzzle and back in response to the pivoting movement of the yoke; and a blade attached to the muzzle end of the blade driver and adapted to move into the muzzle opening to sever a tubular vessel positioned within the muzzle opening when the blade driver moves toward the muzzle.

2. The instrument of claim 1 wherein the trigger further comprises a spring disposed between the trigger and the grip to bias the trigger for return to a rest position at which the ligature driver and blade are withdrawn from the muzzle opening.

3. The instrument of claim 2 wherein the trigger rod is pivotally secured to the trigger.

4. The instrument of claim 2 wherein the spring is further characterized as being disposed around the trigger rod.

5. The instrument of claim 1 wherein the blade driver and blade are integral.

6. The instrument of claim 1 wherein the blade is further characterized to be detachable from the blade driver.

7. The instrument of claim 1 further comprising:
a pair of blade guards pivotally mounted within the barrel proximate to the muzzle opening and shaped to open and close around a vessel positioned in the muzzle opening;

wherein the blade is shaped to have a widened muzzle end and a widened driver end, the widened driver end engaging the blade guards to close the blade guards around the vessel as the blade moves into the muzzle opening, and the widened muzzle end of the blade engaging the blade guards to open the blade guards as the blade is withdrawn from the muzzle opening.

8. The instrument of claim 1 wherein the ligature driver has a pivot pin, the yoke has a ligating slot proximate to the ligating end of the yoke, the pivot pin of the ligature driver extends through the ligating slot of the yoke, and the ligating slot of the yoke is shaped to move the ligature driver toward the muzzle for only a first portion of the pivoting movement of the driver end of the yoke toward the muzzle.

9. The instrument of claim 1 wherein at least a portion of the body is removable to allow access to the cavity in the body.

10. The instrument of claim 1 further comprising:
a ligature container attached to the outer surface of the barrel proximate to the muzzle opening, the container sized and shaped to hold a plurality of ligatures and having an opening to the outer surface of the barrel for disposing one of the ligatures at a time in a position to be pushed by the ligature driver between the ligature compressors to compress the ligature around a tubular vessel positioned in the muzzle opening.

11. The instrument of claim 10 further comprising:
a plurality of ligatures disposed within the ligature container and positioned to be dispensed one at a time to the outer surface of the barrel in a position to be pushed between the ligature compressors by the ligature driver when the ligature driver moves toward the muzzle.

12. The instrument of claim 11 wherein the ligature comprises:
a male leg having an attached end and a locking end;
a female leg having an attached end and a locking end; and
a base connecting the attached end of the male with the attached end of the female leg;
wherein the male leg has a protrusion proximate to the locking end of the male leg and facing the female leg, and the female leg has an aperture mating with the protrusion of the male leg when the male leg and female leg are pressed together.

13. The instrument of claim 11 wherein a plurality of locking rings are formed around the outer periphery of the protrusion of the male leg of each ligature and a locking flange is formed around the aperture of each female leg to grip the locking rings of the protrusion as the protrusion enters the aperture when the male leg and female leg are pressed together.

14. The instrument of claim 11 wherein the base of each ligature has a cutout proximate to the male leg and the female leg to allow substantially full length engagement of the male leg with the female leg when the male leg and female leg are pressed together.

15. The instrument of claim 11 wherein the base of each ligature has a pair ears extending opposite the male leg and female leg, the ears shaped to guide the ligature driver to the base between the ears for pushing the ligature.

16. The instrument of claim 11 wherein the ligatures are stacked within the ligature container and the ligature container is further characterized to include a spring located between the ligatures and the ligature container to bias the ligatures toward the opening of the ligature container.

17. The instrument of claim 11 wherein the ligature container is removably attached to the outer surface of the barrel.

* * * * *

UNITED STATES PATENT AND TRADEMARK OFFICE
CERTIFICATE OF CORRECTION

PATENT NO. : 5,190,560
DATED : March 2, 1993
INVENTOR(S) : John B. Woods et al

It is certified that error appears in the above-indentified patent and that said Letters Patent is hereby corrected as shown below:

Column 1, line 32, change "out" to --cut--.

Column 3, line 5, change "L shaped" to --L-shaped--.

Column 8, line 6, change "15" to --150--.

Column 8, line 57, change "tot he" to --to the--.

Signed and Sealed this

Twenty-eighth Day of December, 1993

Attest:

BRUCE LEHMAN

Attesting Officer    Commissioner of Patents and Trademarks